United States Patent [19]

Kleemann et al.

[11] 4,246,189
[45] Jan. 20, 1981

[54] PROCESS FOR THE PRODUCTION OF HYDROXYNITRILES FROM EPOXIDES AND KETONE CYANOHYDRINS

[75] Inventors: Axel Kleemann, Hanau; Werner Schwarze, Frankfurt, both of Fed. Rep. of Germany

[73] Assignee: Deutsche Gold- und Silber-Scheideanstalt vormals Roessler, Frankfurt, Fed. Rep. of Germany

[21] Appl. No.: 71,025

[22] Filed: Aug. 29, 1979

[30] Foreign Application Priority Data

Sep. 4, 1978 [DE] Fed. Rep. of Germany ....... 2838536

[51] Int. Cl.³ .................. C07C 121/34; C07C 121/75
[52] U.S. Cl. ............................. 260/465 F; 260/465.6
[58] Field of Search ......................... 260/465 F, 465.6

[56] References Cited

U.S. PATENT DOCUMENTS

| | | | |
|---|---|---|---|
| 1,914,326 | 6/1933 | Fick | 260/465.6 |
| 2,390,519 | 12/1945 | Davis et al. | 260/465.6 |
| 2,748,154 | 5/1956 | Journeay | 260/465 F |
| 3,155,601 | 11/1964 | Idol, Jr. | 260/465.6 X |

*Primary Examiner*—Dolph H. Torrence
*Attorney, Agent, or Firm*—Cushman, Darby & Cushman

[57] ABSTRACT

Aliphatic, cycloaliphatic and aromatic epoxides are reacted with ketone cyanohydrins of the formula

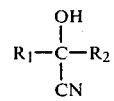

wherein $R_1$ and $R_2$ are aliphatic groups of 1 to 4 carbon atoms at 20° to 150° C. to produce hydroxynitriles. The reaction optionally can be carried out in an inert organic solvent.

26 Claims, No Drawings

PROCESS FOR THE PRODUCTION OF HYDROXYNITRILES FROM EPOXIDES AND KETONE CYANOHYDRINS

BACKGROUND OF THE INVENTION

The class of hydroxynitriles is well known. There are numerous processes for their production. The best known process consists of reacting an epoxide with hydrogen cyanide, according to the general equation

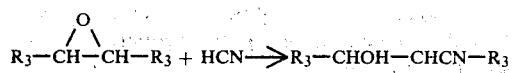

The reaction can be carried out with or without a solvent and if needed with a basic catalyst.

In many cases the reaction must, to be sure, because of the low boiling point of the hydrocyanic acid, be carried out in a closed vessel, i.e., under excess pressure.

The hydrogen cyanide is extraordinarily toxic and the operation must be carried out at great expense for the apparatus in order to carry out this reaction in a normal plant.

The carrying out of such reactions in the technology is forbidden in most cases simply because of the extraordinary problems in the transportation of the hydrogen cyanide.

Besides this mode of action assumes that either there exists a hydrocyanic acid plant or a plant which liberates the hydrocyanic acid from its salts.

The last described method which sets free the hydrocyanic acid from its salts can also be undertaken in the plant itself, but here also extensive precautions must be taken.

In several cases specific epoxides can also be reacted with the salts of hydrogen cyanide itself, e.g., with sodium or potassium cyanide, in suitable solvents, yet in these cases water must always be present. An addition of alkali carbonate then sets free a large part of the hydrocyanic acid from the salt.

Such strongly alkaline solutions containing free hydrocyanic acid are quickly colored dark brown to black through polymerizing hydrocyanic acid.

This also cannot be avoided if the aqueous solutions are mixed, e.g. with alcohols.

Hydroxynitriles which are produced in this way are, insofar as they are solid or crystalline, always contaminated with hydrocyanic acid polymers so that the purification of the reaction products creases large trouble.

The method of using the salts of hydrogen cyanide, in contrast to hydrocyanic acid itself, is not generally usable and is forbidden, e.g. in the reaction of α-epoxides to the corresponding hydroxynitriles.

It has also been proposed already, e.g. to react hydrocyanic acid with acetone to form acetone cyanohydrin, to transport this product to the place of use, to treat it there with alkali and thus to split it again in order to then separate off the hydrocyanic acid by distillation.

All of these procedures always require a great expense.

It has already been proposed by Nazarov, et al (J. Gen. Chem./USSR, 1954, 24, 475 (English Translation), ibid, 1955, 25, 1291) to add hydrocyanic acid with the help of acetone cyanohydrin to an α,β-unsaturated ketone with the help of acetone cyanohydrin; thereby the procedure was such that the ketone was boiled for several hours with a large excess of cyanohydrin in the presence of an aqueous solution of alkali carbonate in alcohol.

The yields then were only satisfactory if no organic bases were used as catalysts.

The reaction speed can be increased if there is chosen a high excess of acetone cyanohydrin and there is used as catalyst a saturated solution of potassium hydroxide in alcohol. B. E. Betts and W. Davey (J. Chem. Soc. 1958, page 4193) demonstrated this as an example of HCN addition on a chalcone.

In Spanish patent 229,413 (Chem. Abst., Vol, 51, page 9723) there is described the addition of HCN via acetone cyanohydrin on 11-oxoprogesterone.

Acetone cyanohydrin is also an efficient selective cyanidization agent for α,β-unsaturated carbonyl compounds if the reaction is carried out in the presence of crown ethers and potassium or sodium cyanide in polar or nonpolar solvents (Liotta, et al, Tetrahedron Letters, 1977, page 1117, et seq).

In all the previously described processes, it is a matter of adding hydrocyanic acid to α,β-unsaturated compounds.

It is the purpose of the present invention to add hydrocyanic acid to an epoxide by a dangerless and environmentally favorable process.

SUMMARY OF THE INVENTION

It has now been found that hydroxynitriles can be produced in good to very good yields and in an industrially simple and dangerless manner if aliphatic, cycloaliphatic or aromatic epoxides are reacted with ketone cyanohydrins of the general formula

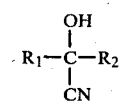

in which $R_1$ and $R_2$ are aliphatic groups, e.g. alkyl groups with 1 to 4 carbon atoms, e.g. methyl, ethyl, propyl, butyl, isopropyl, sec. butyl and $R_1$ and $R_2$ can be the same or different, at temperatures of 20° to 150° C. in alkaline medium at a pH of above 7 to 14 wherein the reaction in a given case is carried out in the presence of an inert organic solvent.

The described reaction proceeds according to the general formula

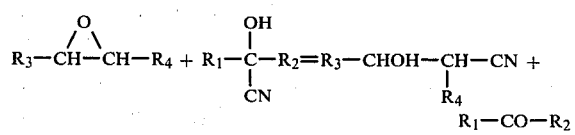

The preferred ketone cyanohydrins are acetone cyanohydrin, methyl ethyl ketone cyanohydrin, methyl isopropyl ketone cyanohydrin and/or methyl isobutyl ketone cyanohydrin. Acetone cyanohydrin is preferred.

Additional cyanohydrins include dibutyl ketone cyanohydrin, diethyl ketone cyanohydrin, methyl sec. butyl ketone cyanohydrin.

As epoxides there are employed those of the general formula

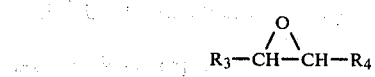

where $R_3$ and $R_4$ are hydrogen or alkyl groups with 1 to 24 carbon atoms which can be substituted by OH, S or Cl as well as aryl groups and haloaryl groups, e.g. chloroaryl, fluoroaryl or bromoaryl, which alkyl or aryl groups can be substituted by -O-alkyl, -O-aryl, O-haloaryl, -S-alkyl or -S-aryl. The alkyl substitutes are usually lower alkyl.

Examples of epoxides are ethylene oxide, propylene oxide, butylene oxide, 1,2-epoxyoctane, 1,2-epoxydecane, 1,2-epoxydodecane, 1,2-epoxyoctadecane, 1,2-epoxyeicosane, 1,2-epoxytetraeicosane, epichlorohydrin, glycide (glycidol), glycidyl monomethyl ether, glycidyl monoethyl ether, glycidyl monophenyl ether, 3-methylthio-1,2-epoxypropane, 3-ethylthio-1,2-epoxypropane, 3-phenylthio-1,2-epoxypropane, 4-methylthio-1,2-epoxybutane, styrene oxide, 3-phenoxy-1,2-epoxypropane, 3-(4-chlorophenoxy)-1,2-epoxypropane or 3-naphthoxy-1,2-epoxypropane.

Additional epoxides include 1,2-epoxyhexaeicosane, 2,3-epoxybutane, 2,3-epoxydecane, 5,6-epoxydodecane, glycidyl monobutyl ether, glycidyl monodecyl ether, p-methystyrene oxide, p-chlorostyrene oxide, glycidyl 3-(4-bromophenoxy)-1,2-epoxy propane, 3-(2,4-dichlorophenoxy)-1,2-epoxypropane, 3-(4-methylphenoxy)-1,2-epoxypropane, 3-(4-methylphenoxy-1,2-epoxypropane, 4-methoxy-1,2-epoxybutane, 3-phenylthio-1,2-epoxy propane, 3-cyclohexoxy-1,2-epoxypropane, 3-dodecyloxy-1,2-epoxypropane, p-methoxyphenoxy-1,2-epoxypropane.

Especially preferred epoxides are propylene oxide, 1,2-epoxyoctane or 3-phenoxy-1,2-epoxypropane.

The ketone cyanohydrins and epoxides are reacted in equimolar ratios, preferably with an excess of ketone cyanohydrin of about 5 to 20 mole %.

For regulating the pH there can be used tertiary aliphatic e.g., alkyl or even araliphatic amines, which amines also can be used as mixtures. Illustrated amines are trimethyl amine, triethylamine, tri-isopropylamine, tributylamine, dicyclohexyl methyl amine, dodecyl dimethyl amine, tribenzylamine, dimethyl ethyl amine.

Likewise for this purpose there can be used alkali alcoholates with 1 to 4 carbon atoms, e.g. sodium methylate, potassium methylate, sodium ethylate, potassium ethylate, sodium propylate, sodium butylate, potassium butylate or even alkali cyanide, e.g. sodium cyanide and potassium cyanide. By the term alkali there is understood sodium and potassium.

As organic solvents whose boiling range lies within the stated range of 20° to 150° C. (for the reaction) there can be mentioned: aliphatic alcohols with 1 to 4 carbon atoms, e.g., alkanols such as methanol, ethanol, isopropanol, propanol, n-butanol, sec-butyl alcohol, or esters of these alcohols with lower aliphatic carboxylic acids, e.g. alkanoic acids, such as e.g., methyl acetate, methyl propionate, ethyl propionate, methyl butyrate, as well as higher molecular weight aliphatic hydrocarbons such as pentane, hexane, heptane, octane, including their isomers, e.g., isooctane, as well as nonane or mixtures of these aliphatic hydrocarbons, additionally aromatic hydrocarbons such as tetramethyl benzene or mixtures of different alkylated benzenes such as diethyl benzene, dipropyl benzene as well as halogenated derivatives of lower aliphatic hydrocarbons such as dichloro compounds of methane to butane e.g., methylene chloride 1,2-dichloroethane, 1,1-dichloroethane, 1,3-dichloropropane, 1,4-dichlorobutane.

Preferred are methanol and the propanols. Expecially preferred, however, are ketones which corresponds to the ketone cyanohydrins employed and which are obtained after the reaction with the epoxides, above all acetone, methyl ethyl ketone, methyl isopropyl ketone and methyl isobutyl ketone.

The hydroxynitriles are known interesting intermediate products; e.g., the long chain aliphatic hydroxynitriles are saponified to hydroxycarboxylic acids, which in turn have interesting surfactant properties.

If the hydroxynitriles are hydrogenated there are obtained hydroxyalkyl amines which inter alia are interesting building blocks for heterocyclic systems.

The advance in the art of the process of the invention is that the hydroxynitrile can be recovered in a technically simple manner from easily accessible and easily handlable starting materials.

Besides the hydroxynitriles are obtained in pure form and in high yield.

Since in the claimed process free hydrocyanic acid always occurs only in low concentration, the hydroxynitriles formed are predominantly practically free from polymeric impurities. This condition could not have been predicted since the hydrogen cyanide intermediate always formed in the reaction is immediately added on the epoxide ring.

Besides the process is very favorable to the environment.

The process can comprise, consist essentially of or consist of the steps set forth and the materials employed can comprise, consist essentially of or consist of those set forth.

Unless otherwise indicated all parts and percentages are by weight.

The process will be explained further in connection with the following examples.

DESCRIPTION OF THE PREFERRED EMBODIMENTS

EXAMPLE 1

There were placed in a 1 liter three necked round bottom flask 260 grams of acetone cyanohydrin, 300 ml of methanol and 174 grams of propylene oxide.

There were added thereto with stirring 2 ml of triethylamine so that the pH of the mixture was about 9, stirring was carried out first for 30 minutes at 20° C. and subsequently for 10 hours between 50° and 60° C. Subsequently this mixture was fractionated on a 1 meter Vigreux column.

At B.P.$_{11}$ 102° to 104° C. there distilled 3-hydroxybutyronitrile, amount 207.1 grams, corresponding to 81.2% of theory as a colorless oil.

EXAMPLE 2

1.2 kg of styrene oxide and 1.5 liters of isopropanol were mixed with 900 grams of acetone cyanohydrin, subsequently there were added 5 grams of tributylamine (pH of the mixture 9.5) and subsequently heated for 12 hours at 80° C. The mixture was subsequently worked up by distillation.

At B.P.$_{12}$ 147 to 149 there distilled 3-phenyl-3-hydroxypropionitrile in an amount of 1.14 kg, corresponding to 78% of theory.

EXAMPLE 3

There were mixed 128 grams of 1,2-epoxyoctane and 90 grams of acetone cyanohydrin and then the mixture treated with 2 grams of tributylamine, through which the pH of 9.8 was attained.

The mixture was heated at 60° C. for 14 hours, cooled, diluted with methylene chloride, washed with water, dried and the solvent evaporated in a vacuum. A light yellow semicrystalline product remained behind. Amount 141 grams.

| Analysis | Found: | C 69.6 | H 10.7 | N 8.95 |
|---|---|---|---|---|
| $C_9H_{17}NO$ | Calculated: | 70 | 11 | 9.00 |
| (mol wt. 155) | | | | |
| Yield: based on Hydroxynitrile: 91% of theory | | | | |

EXAMPLE 4

In an analogous manner to the reaction with 1,2-epoxyoctane in Example 3 there were reacted the following 1,2-epoxides.

| Starting Material | End Product | M.P. | Yield |
|---|---|---|---|
| $C_{10}H_{21}$—CH—CH$_2$ (epoxide) | $C_{10}H_{21}$—CHOH—CH$_2$—CN | | 98.1% |
| $C_{16}H_{33}$—CH—CH$_2$ (epoxide) | $C_{16}H_{33}$—CHOH—CH$_2$—CN | 51° C. | 100% |

EXAMPLE 5

1.5 kg of 3-phenoxy-1,2-epoxypropane and 1.5 liters of acetone were mixed, there were added thereto 900 grams of acetone cyanohydrin. The pH was adjusted to about 9 with triethylamine (3 ml). The mixture was heated at 55° C. for 3 hours, then the reaction was over.

The acetone was then distilled off at normal pressure (atmospheric pressure). There resulted an oil which quickly thoroughly crystallized, M.P. 49° to 50° C.

The working up produced 2-hydroxy-3-phenoxybutyronitrile, cream colored crystals, amount:1.74 kg=98% of theory.

EXAMPLE 6

The following 3-aryloxy-1,2-epoxypropanes were reacted in a manner corresponding to the directions of Example 5.

| Starting Material | End Product | M.P. | Yield |
|---|---|---|---|
| Cl—C₆H₄—O—CH₂—CH—CH₂ (epoxide) | Cl—C₆H₄—O—CH₂—CHOH—CH₂—CN | 59–61° C. | 99.3% |
| Cl—C₆H₃(Cl)—O—CH₂—CH—CH₂ (epoxide) | Cl—C₆H₃(Cl)—O—CH₂—CHOH—CH₂—CN | 80–81° C. | 100% |
| Naphthyl—O—CH₂—CH—CH₂ (epoxide) | Naphthyl—OCH₂—CHOH—CH₂—CN | 88° C. | 87.3% |

EXAMPLE 7

925 grams of epichlorhydrin, 500 ml of acetone and 935 grams of acetonecyanohydrin were adjusted to a pH of 8.5 with the help of dodecyl dimethyl amine and boiled at reflux for 12 hours. Working up by distillation yielded 3-hydroxy-4-chlorobutyronitrile, B.P.$_{11}$ 136° to 138° C. Amount 801.8 grams corresponding to 67% of theory.

EXAMPLE 8

The reaction of 3-phenoxy-1,2-epoxypropane to 2-hydroxy-3-phenoxybutyronitriles was carried out with various ketone cyanohydrins common addition:

| Common addition: | 3-phenoxy-1,2-epoxypropane | 1 mole |
|---|---|---|
| | ketone cyanohydrin | 1.05 mole |
| | methanol | 100 ml |
| | triethylamine | 1–2 ml |

| Cyanohydrin | I.React. Time | II.Temp. | III.Yield |
|---|---|---|---|
| Methylethylketone cyanohydrin | 6 hours | 55° C. | 96.7% |
| Methylisopropylketone cyanohydrin | 9 hours | 65° C. | 94.0% |
| Methylisobutylketone cyanohydrin | 16 hours | 80° C. | 94.3% |

There is hereby incorporated by reference German priority application No. P 2838536.6.

What is claimed is:

1. Process for the production of a hydroxynitrile comprising reacting an aliphatic, cycloaliphatic or aromatic epoxide with a ketone cyanohydrin of the formula

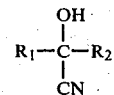

where $R_1$ and $R_2$ are 1 to 4 carbon atom alkyl groups in an alkaline medium at 20° to 150° C., the structure of the hydroxynitrile being derived from the epoxide except that the nitrile group is derived from the ketone cyanohydrin.

2. The process of claim 1 wherein the reaction is carried out in the absence of a solvent.

3. The process of claim 1 which is carried out in the presence of an inert organic solvent.

4. The process of claim 1 wherein the epoxide has the formula

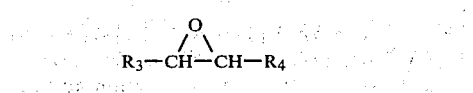

where $R_3$ and $R_4$ are hydrogen; alkyl of 1 to 24 carbon atoms; alkyl of 1 to 24 carbon atoms substituted by OH, S, aryl, haloaryl, Cl, O-alkyl, O-aryl, O-haloaryl, S-alkyl, or S-aryl; aryl; haloaryl; aryl-O-aryl, aryl-O-haloaryl, aryl-S-alkyl or aryl-S-aryl, said hydroxynitrile having the formula

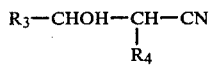

5. The process of claim 1 wherein the epoxide is ethylene oxide, propylene oxide, butylene oxide, 1,2-epoxyoctane, 1,2-epoxydecane, 1,2-epoxydodecane, 1,2-epoxyoctadecane, 1,2-epoxyeicosane, 1,2-epoxytetraeicosane, epichlorhydrin, glycidol, glycidolmonomethyl ether, glycidol monoethyl ether, glycidol monophenyl ether, 3-methylthio1,2-epoxypropane, 3-ethylthio-1,2-epoxypropane, 3-phenylthio-1,2-epoxypropane, 4-methylthio-1,2-epoxybutane, styrene oxide, 3-phenoxy-1,2-epoxypropane, 3-(4-chlorophenoxy)-1,2-epoxypropane, 3-naphthoxy-1,2-epoxypropane.

6. The process of claim 5 wherein the epoxide is propylene oxide, 1,2-epoxyoctane, or 3-phenoxy-1,2-epoxypropane.

7. The process of claim 6 wherein the cyanohydrin is acetone cyanohydrin, methyl ethyl ketone cyanohydrin, methyl isopropyl ketone cyanohydrin or methyl isobutyl ketone cyanohydrin.

8. The process of claim 5 wherein the cyanohydrin is acetone cyanohydrin, methyl ethyl ketone cyanohydrin, methyl isopropyl ketone cyanohydrin or methyl isobutyl ketone cyanohydrin.

9. The process of claim 4 wherein the cyanohydrin is acetone cyanohydrin, methyl ethyl ketone cyanohydrin, methyl isopropyl ketone cyanohydrin or methyl isobutyl ketone cyanohydrin.

10. The process of claim 9 wherein the ketone cyanohydrin is acetone cyanohydrin.

11. The process of claim 8 wherein the ketone cyanohydrin is acetone cyanohydrin.

12. The process of claim 7 wherein the ketone cyanohydrin is acetone cyanohydrin.

13. The process of claim 7 wherein the ketone cyanohydrin is added in an excess of 5 to 20 mole % above the equivalent proportion to the epoxide.

14. The process of claim 5 wherein the ketone cyanohydrin is added in are excess of 5 to 20 mole % above the equivalent proportion to the epoxide.

15. The process of claim 4 wherein the ketone cyanohydrin is added in an excess of 5 to 20 mole % above the equivalent proportion to the epoxide.

16. The process of claim 4 wherein the sole reactants added are the ketone cyanohydrin and the epoxide.

17. The process of claim 4 wherein the pH of the reaction solution is adjusted with a tertiary aliphatic amine or a tertiary araliphatic amine.

18. The process of claim 4 wherein the pH of the reaction solution is adjusted with an alkali alcoholate with 1 to 4 carbon atoms or an alkali cyanide.

19. The process of claim 4 wherein the reaction is carried out in the presence of a ketone of the formula $R_1$–CO–$R_2$ as a solvent where $R_1$ and $R_2$ are alkyl of 1 to 4 carbon atoms.

20. The process of claim 19 where the ketone solvent is the same ketone used to form the ketone cyanohydrin.

21. The process of claim 20 wherein the ketone is acetone.

22. The process of claim 4 wherein the reaction is carried out in a solvent which is an alkanol with 1 to 4 carbon atoms or a lower alkyl ester of an alkanoic acid.

23. The process of claim 4 wherein the reaction is carried out in the presence of a high molecular weight aliphatic, cycloaliphatic or aromatic hydrocarbon.

24. The process of claim 4 wherein the reaction is carried out in a solvent which is a halogenated lower aliphatic hydrocarbon.

25. The process of claim 4 wherein $R_3$ is aryl, alkyl or 1 to 24 carbon atoms, methyl substituted by OH, O-aryl, O-haloaryl or halo and $R_4$ is hydrogen.

26. The process of claim 4 wherein the epoxide is propylene oxide, styrene oxide, 1,2-epoxyoctane, 1,2-epoxydodecane, 1,2-epoxyoctadecane, 3-phenoxy-1,2-epoxypropane, 3-(4-chlorophenoxy)-1,2-epoxypropane, 3(2,4-dichlorophenoxy)-1,2-epoxypropane, 3-naphthoxy-1,2-epoxypropane, 3-phenoxy-1,2-epoxypropane, epichlorohydrin.

* * * * *